US006759242B1

(12) United States Patent
Csete et al.

(10) Patent No.: US 6,759,242 B1
(45) Date of Patent: Jul. 6, 2004

(54) LOW OXYGEN CULTURING OF NEURAL CREST STEM CELLS AND METHODS OF USE

(75) Inventors: Marie Csete, S. Pasadena, CA (US); Sean J. Morrison, Ann Arbor, MI (US); Barbara Wold, San Marino, CA (US); David J. Anderson, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/425,624

(22) Filed: Oct. 22, 1999

Related U.S. Application Data

(63) Continuation-in-part of application No. 09/195,569, filed on Nov. 18, 1998, now Pat. No. 6,184,035.

(51) Int. Cl.[7] .............................. C12N 5/00; C12N 5/06; C12N 5/08
(52) U.S. Cl. ....................... 435/368; 435/375; 435/377; 435/383
(58) Field of Search ................................. 435/375, 368, 435/377, 383

(56) References Cited

U.S. PATENT DOCUMENTS

| | | | |
|---|---|---|---|
| 5,328,695 A | | 7/1994 | Lucas et al. ................. 424/426 |
| 5,550,050 A | | 8/1996 | Holland et al. ........... 435/240.2 |
| 5,728,581 A | | 3/1998 | Schwartz et al. ........... 435/385 |
| 5,750,103 A | * | 5/1998 | Cherksey ................. 424/93.21 |
| 5,750,376 A | | 5/1998 | Weiss et al. ............. 435/69.52 |
| 6,033,906 A | * | 3/2000 | Anderson .................... 435/325 |

OTHER PUBLICATIONS

Sorokan et al. Molecular Biology of the Cell. 1996. vol. 7, Suppl. p. 317a.*
Nurse et al. Developmental Biology. 1997. vol. 184, pp. 197–206.*
Haavik et al. Mol.neurobiol.1998, 16(3), pp. 285–309.*
Fraser, et al., "Migrating neural crest cells in the trunk of the avian embryo are multipotent," *Development*, 112:913–920 (1991).
Stemple, et al., "Isolation of a stem cell for neurons and glia from the mammalian neural crest," *Cell* 71:973–985 (1992).
Varley, et al., "Number of adrenergic and islet–1 immunoreactive cells is increased in avian trunk neural crest cultures in the presence of human recombinant osteogenic protein–1," *Dev. Dynam.* 203:434–447 (1995).
Varley, et al., BMP–2 and BMP–4, but not BMP–6, increase the number of adrenergic cells which develop in quail trunk neural crest cultures, *Exp. Neurol.* 140:84–94 (1996).
Reissman, et al., "Involvement of bone morphogenetic protein–4 and bone morphogenetic protein–7 in the differentiation of the adrenergic phenotype in developing sympathetic neurons," *Development* 122:2079–2088 (1996).

Lo, et al., "Specification of neurotransmitter identity by Phox2 proteins in neural crest stem cells," *Neuron*. 22:693–705 (1999).
Shah, et al., "Alternative neural crest cell fates are instructively promoted by TGF superfamily members," *Cell* 85:331–343 (1996).
Gage, et al., "CNS grafting: potential mechanisms of action," *Neural Regeneration and Transplantation*, 211–226 (Alan R. Liss, Inc., New York, 1989).
Freed, et al., "Survival of implanted fetal dopamine cells and neurologic improvement 12 to 46 months after transplantation for Parkinson's disease," *New England Journal of Medicine*, 327:1549–1555 (1992).
Date, I., "Parkinson's disease, trophic factors, and adrenal medullary chromaffin cell grafting: basic and clinical studies," *Brain Research Bulletin* 40:1–19 (1996).
Luquin, et al., "Recovery of chronic parkinsonian monkeys by autotransplants of carotid body cell aggregates into putamen," *Neuron* 22:743–750 (1999).
Stoddard, et al., "Decreased adrenal medullary catecholamines in adrenal transplanted parkinsonian patinets compared to nephrectomy patinets," *Experimental Neurology* 104:218–222 (1989).
Zawada, et al., "Somatic cell cloned transgenic bovine neurons for transplantation in parkinsonian rats," *Nature Medicine* 4:569–574 (1998).
Studer, et al., "Transplantation of expanded mesencephalic precursors leads to recovery in parkinsonian rats," *Nature Neuroscience* 1:290–295 (1998).
Pentland and Marcelo, "Modulation of Proliferation in Epidermal Keratinocyte Cultures by Lowered Oxygen Tension," *Exp Cell Res* 145:31–43 (1983).
Cipolleschi et al., "The Role of Hypoxia in the Maintenance of Hematopoietic Stem Cells," *Blood* 82(7):2031–2037 (1993).
Colton, et al., "Protection from Oxidation Enhances the Survival of Cultured Mesencephalic Neurons," *Experimental Neurology*, 132:54–61 (1995).
Nurse, et al., "Role of Basic FGF and Oxygen in Control of Proliferation, Survival, and Neuronal Differentiation in Carotid Body Chromaffin Cells," *Developmental Biology*, 184:197–206 (1997).
Czyzyk–Krzeska, et al., "Hypoxia Increases Rate of Transcription and Stability of Tyrosine Hydroxylase mRNA in Pheochromocytoma (PC12) Cells," *The Journal of Biological Chemistry*, 269(1):760–764 (1994).

(List continued on next page.)

*Primary Examiner*—Sandra E. Saucier
*Assistant Examiner*—Vera Afremova
(74) *Attorney, Agent, or Firm*—Richard F. Trecartin; David C. Foster; Dorsey & Whitney LLP

(57) ABSTRACT

The present invention relates to the growth of cells in culture under conditions that promote differentiation, cell survival, and/or cellular proliferation. More particularly, culturing neural crest stem cells in low oxygen conditions is described.

24 Claims, 5 Drawing Sheets-

OTHER PUBLICATIONS

Brewer, et al., "Survival and Growth of Hippocampal Neurons in Defined Medium at Low Density Advantages of a Sandwich Culture Technique of Low Oxygen," *Brain Research* 494:65–74 (Abstract) (1989).

Koller, et al., "Effects of Synergistic Cytokine Combinations, Low Oxygen, and Irradiated Stroma on the Expansion of Human Cord Blood Progenitors," *Blood* 80(2):402–411 (1992).

Potocnik, "In vitro generation of lymphoid precursors from embryonic stem cells," *The EMBO Journal* 13(22):5274–5283 (1994).

Kagamu, et al., "Low Oxygen Enhances Endothelin–1 (ET–1) Production and Responsiveness to ET–1 in Cultured Cardiac Myocytes," *Biochemical and Biophysical Research Communications*, 202(3):1612–1618 (1994).

Sosa, et al., "Isolation and Long-term Survival of Adult Human Sensory Neurons In Vitro," *Neurosurgery*, 42(3):681–686 (1998).

Takahasi, et al., "Effect of Chronic Hypoxia on Skeletal Muscle Fiber Type in Adult Male Rats," *Ann. Physiol. Anthrop.* 11(6):625–630 (1992).

Metcalfe, et at., "Stimulation of extraocular muscle fibroblasts by cytokines and hypoxia: possible role in thyroid–associated ophthalmopathy," *Clinical Endocrinology* 40:67–72 (1994).

Robin, et al., "Coordinate Regulation of Glycolysis by Hypoxia in Mammalian Cells," *Journal of Cellular Physiology*, 118:287–290 (1984).

Darinskii, et al., "Effect of the Conditions of Antenatal Development on Functional Maturation of Rabbit Fetal Skeletal Muscle," *Bulletin of Experimental Biology and Medicine*, 77(2):104–106 (1974).

Kuzin, et al., "Nitric Oxide Regulates Cell Proliferation during Drosophila Development," *Cell* 87:639–649 (1996).

Pentland, et al., "Effects of Gas Tension on Epidermal Keratinocyte DNA Synthesis and Prostaglandin Production," *The Journal of Investigative Dermatology* 86(2):177–180 (1986).

Horikoshi, et al., "Effect of Oxygen on the Growth of Human Epidermal Keratinocytes," *The Journal of Investigative Dermatology* 86(4):424–427 (1986).

Storch, "Oxygen Concentration Regulates 5–azactidine–induced myogenesis in $C_3H/10T1/2$ cultures," *Biochimica et Biophysica Acta*. 1055:126–129 (1990).

Cornelison, et al., "Single–Cell Analysis of Regulatory Gene Expression in Quiescent and Activated Mouse Skeletal Muscle Satellite Cells," *Developmental Biology* 191:270–283 (1997).

Genbacev, et al., "Regulation of Human Placental Development by Oxygen Tension," *Science* 277:1669–1672 (1997).

Iyer, et al., *Genes and Development* 12:149–162 (1998).

Sorokan et al, *Molecular Biology of the Cell* 7(Suppl.):317A.

Birren, et al., "Sympathetic neuroblasts undergo a developmental switch in trophic dependence," *Development* 119:597–610 (1993).

Morrison, et al, "Prospective identification, isolation by flow cytometry, and in vivo self–renewal of multipotent mammalian neural crest stem cells," *Cell* 96:737–749 (1999).

Verdi, et al., "Neurotrophins regulate sequential changes in neurotrophin receptor expression by sympathetic neuroblasts," *Neuron* 13:1359–1372 (1994).

Yamamori, et al., "The cholinergic neuronal differentiation fator from heart cells is identical to leukemia inhibitory factor," *Science* 246:1412–1416 (1989).

Blancher, et al., "The molecular basis of the hypoxia response pathway: tumor hypoxia as a therapy target," *Cancer and Metastasis Reviews* 17:187–194 (1998).

Czyzyk–Krzeska,et al., "Regulation of tyrosine hydroxylase gene expression in the rat carotid body by hypoxia," *Journal of Neurochemistry* 58:1538–1546 (1992).

Doupe, et al., "Environmental Influences in the Development of Neural Crest Derivatives: Glucocorticoids, growth factors and chromaffin cell plasticity," *J. Neurosci.* 5:2119–2142 (1985).

Doupe, et al., "Small intensely fluorescent (SIF) cells in culture: role of glucocorticoids and growth factors in their development and phenotypic interconversions with other neural crest derivatives," *J. Neurosci.* 5:2143–2160 (1985).

Anderson, D.J., "Molecular control of cell fate in the neural crest: the sympathoadrenal lineage," *Annu. Rev. Neurosci.* 16:129–158 (1993).

\* cited by examiner

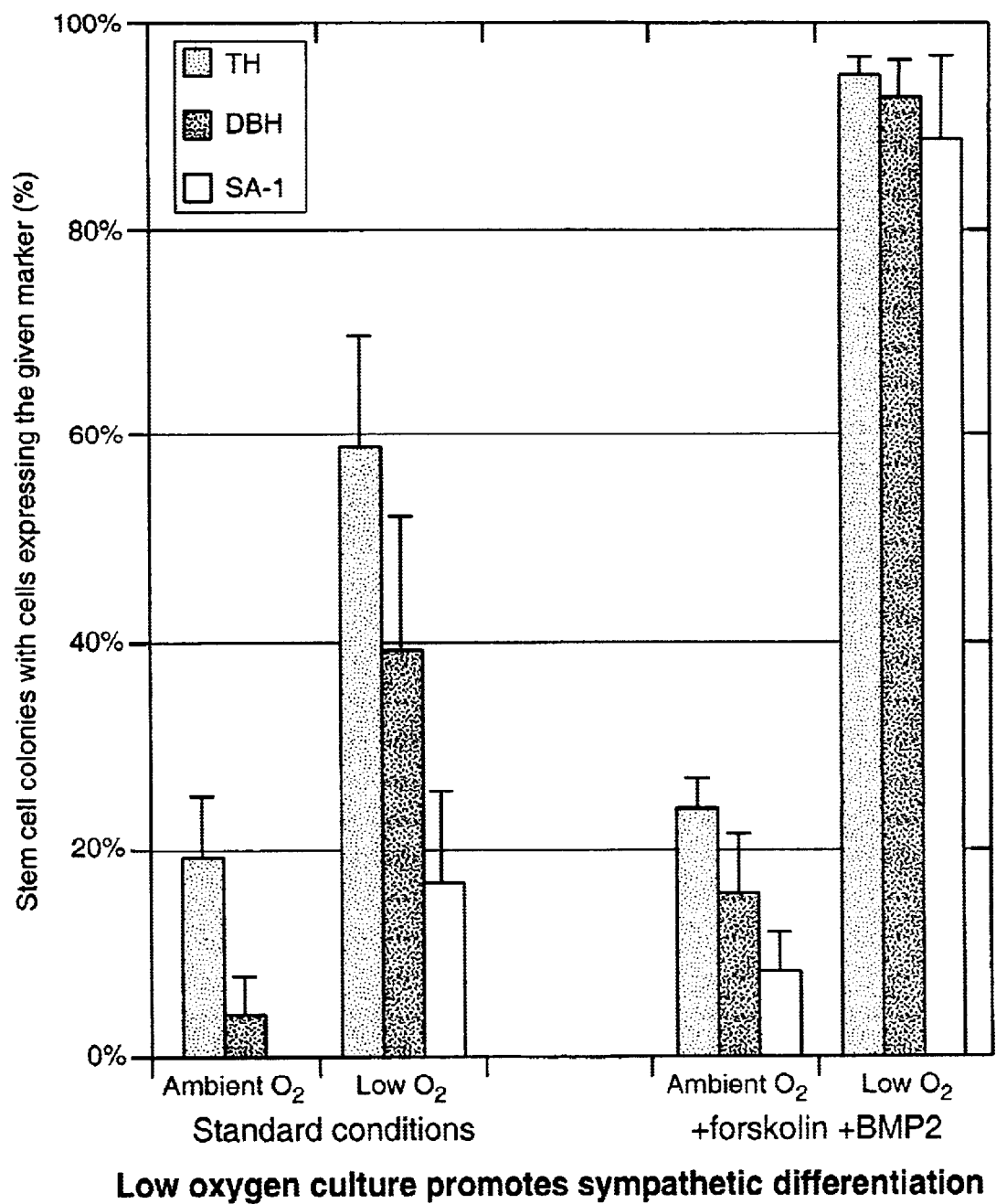
Low oxygen culture promotes sympathetic differentiation
FIG._1

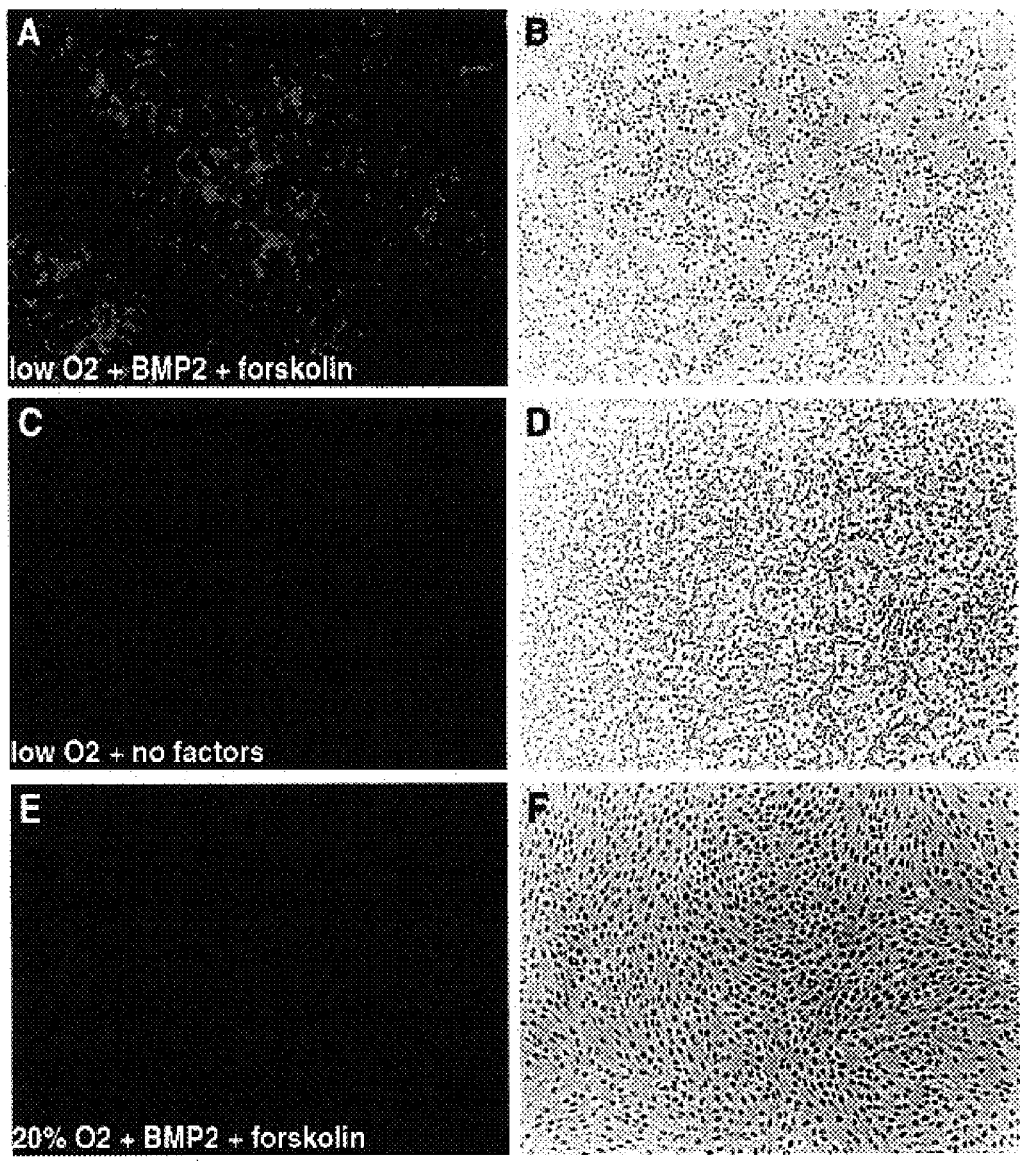
FIG._2

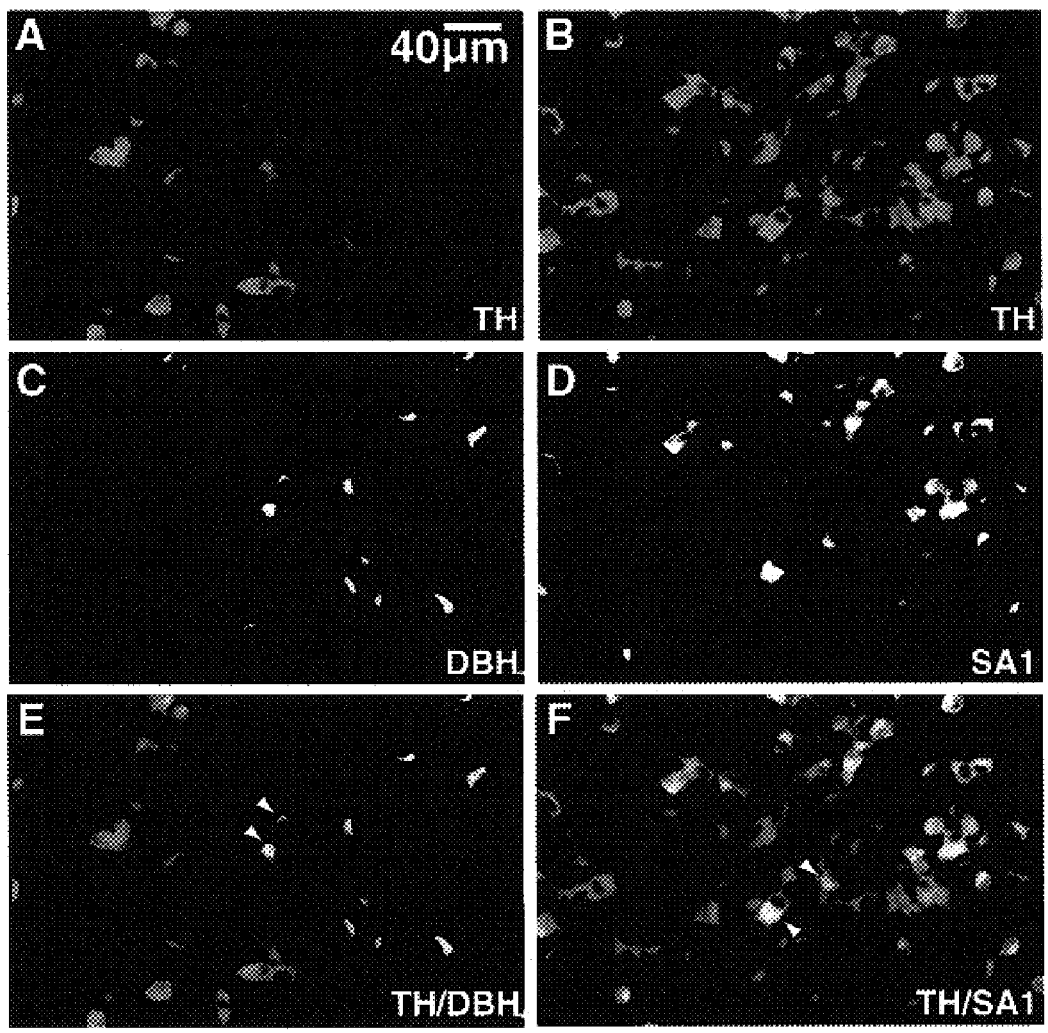
FIG._3

Colony 1 TH/NFM
Colony 2 TH/NFM
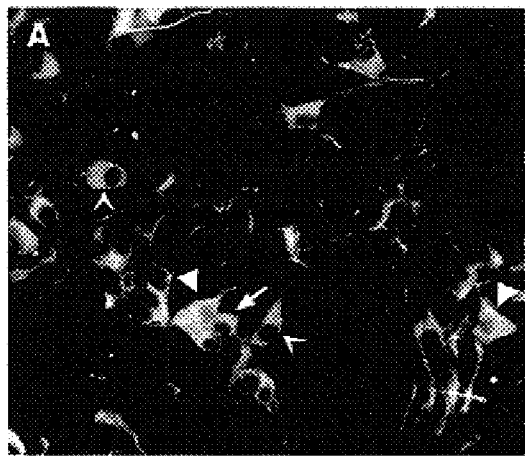
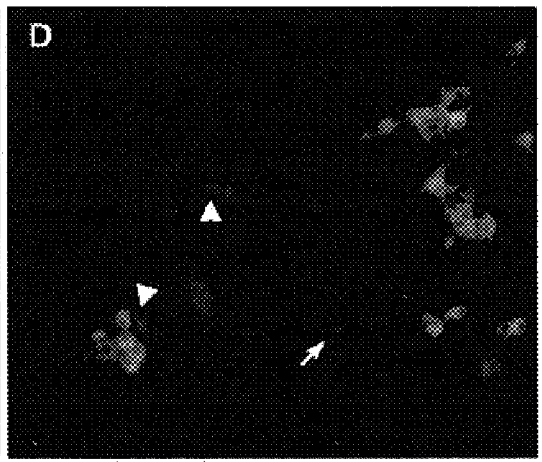
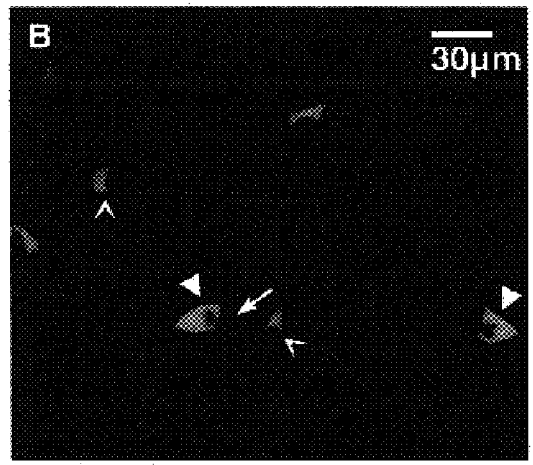
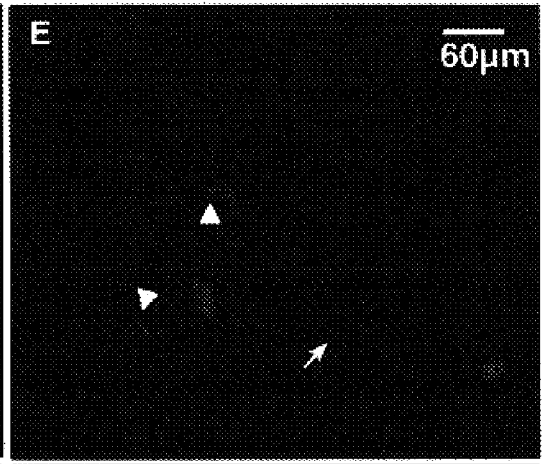
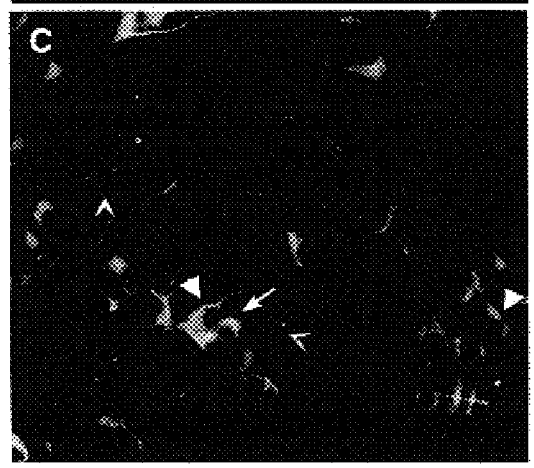
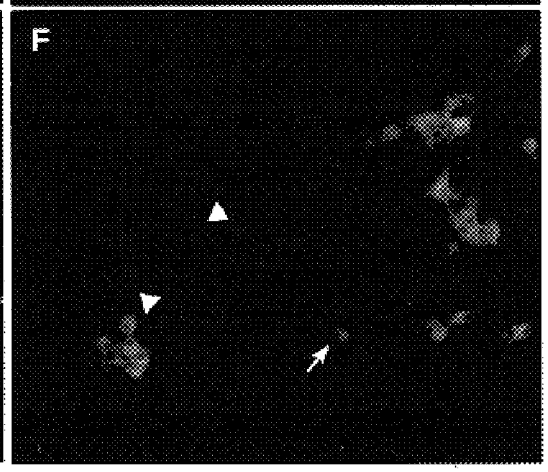
FIG._4

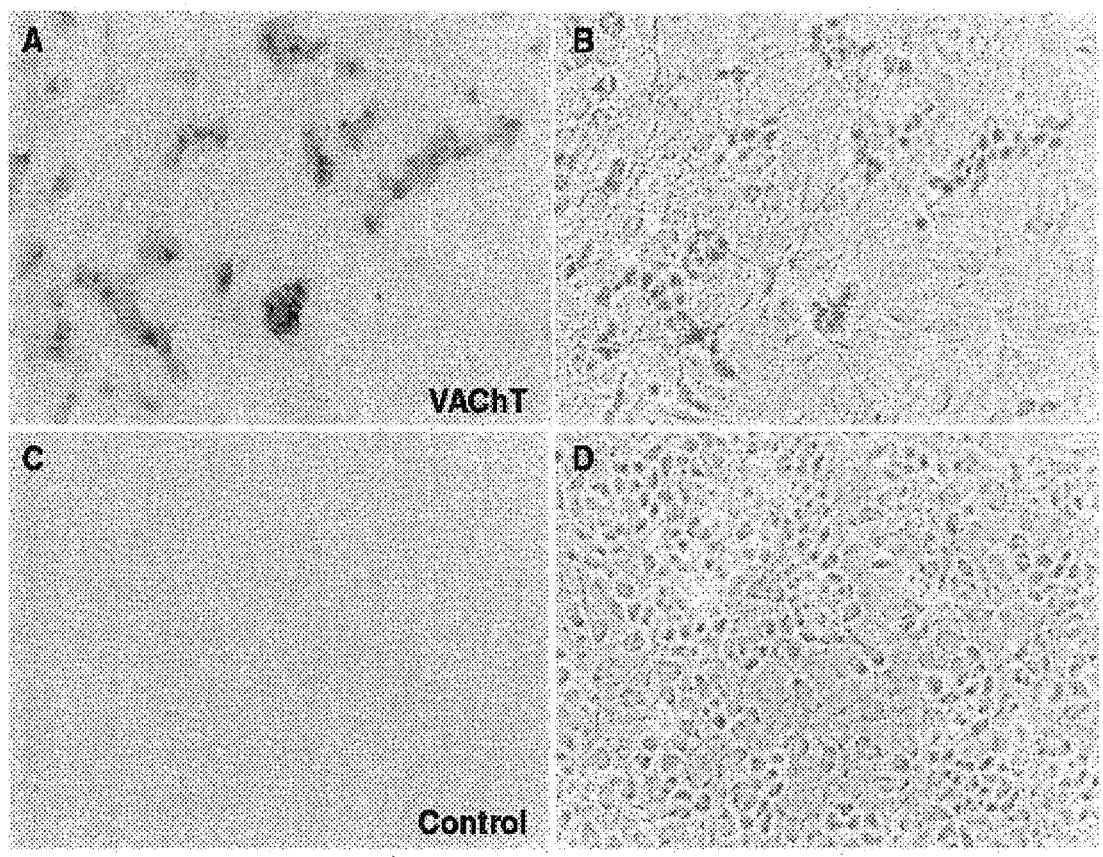
FIG._5

LOW OXYGEN CULTURING OF NEURAL CREST STEM CELLS AND METHODS OF USE

RELATED APPLICATIONS

The present application is a continuation-in-part of U.S. application Ser. No. 09/195,569 filed Nov. 18, 1998 now U.S. Pat. No. 6,184,035. The entire text and all references cited therein of the above referenced application are incorporated herein by reference without prejudice or disclaimer.

FIELD OF THE INVENTION

The present invention relates to the growth of cells in culture. More particularly, the present invention provides methods and compositions for increasing cell survival, cell proliferation and/or cell differentiation along specific pathways by growing the cells in low ambient oxygen conditions.

BACKGROUND OF THE INVENTION

The sympathoadrenal (SA) lineage of the neural crest gives rise to all of the catecholaminergic derivatives of the peripheral nervous system (PNS). These include sympathetic neurons, adrenal chromaffin cells, carotid body cells, and Small Intensely Fluorescent (SIF) cells (Doupe, et al., 1985, at p. 2119 and p. 2143). The terminal differentiation and plasticity of SA derivatives have been intensively studied for over a decade (reviewed in Anderson, et al., 1993). Although multipotent neural crest progenitors have been observed to give rise to SA derivatives in vivo (Fraser, 1991), relatively little is known about how neural crest stem cells (NCSCs) become committed to this sublineage. Bone Morphogenetic Proteins (BMPs) -2, -4 and -7 have been identified as inducers of SA marker expression in mass cultures of avian and mammalian neural crest cells (Varley, et al., 1995; Varley, et al., 1996; Reissman, et al, 1996; and Lo, et al., 1999). Such BMPs can also induce autonomic neuron differentiation in clonal cultures of mammalian NCSCs (Stemple, 1992), but they do not induce SA lineage markers (Shah, et al., 1996). The inability to achieve SA lineage differentiation in clonal cultures of NCSCs has severely hampered further study of the mechanisms regulating this important lineage restriction process.

The sympathetic potential of NCSCs is of clinical as well as basic interest because sympathetic lineage cells synthesize dopamine and dopaminergic cells are used to alleviate Parkinson's disease (reviewed in Gage, et al., 1989). Parkinson's disease is a relatively common neurodegenerative disorder caused by the loss of dopaminergic neurons in the substantia nigra. The transplantation of a wide variety of dopaminergic cell types, including fetal mesencephalon (Freed, et al., 1992) and neural crest-derived adrenal chromaffin cells (Date, 1996) or carotid body cells (Luquin, 1999) into the substantia nigra can ameliorate the symptoms of Parkinson's disease; however, the supply of fetal tissue is very limited and even autologous transplants of dopaminergic cells may sometimes be unsuitable (Date, 1996; Stoddard, et al., 1989). These constraints have prompted extensive efforts to identify alternate sources of dopaminergic neurons (Zawada, 1998) and to expand dopaminergic cells in culture (Studer, 1998).

Therefore, it is desirable to understand the differentiation pathways of neural crest stem cells. Moreover, it is desirable to provide methods of enhancing differentiation, proliferation and/or survival of neural crest stem cells. Furthermore, it is desirable to expand stem cell or progenitor numbers in culture and form neurons in culture, particularly dopaminergic or noradrenergic neurons in culture.

BRIEF SUMMARY OF THE INVENTION

The present invention is directed to growing cells in low ambient oxygen conditions in order to mimic the physiological oxygen conditions with greater fidelity. The growth of these cells in such conditions provides certain surprising and unexpected results. These results are exploited and described in further detail herein. More particularly, the present invention describes methods that may independently be useful in increasing cell survival, cell proliferation and/or cell differentiation along specific pathways.

In one embodiment, a method of culturing at least one neural crest stem cell (NCSC) to enhance survival, proliferation or differentiation of the NCSC is provided. The method comprises culturing the NCSC(s) in low ambient oxygen conditions, wherein said survival, proliferation or differentiation is enhanced compared to a control NCSC cultured in ambient oxygen conditions.

In one aspect, a method is provided for enhancing differentiation of the NCSC wherein differentiation is to a neuron. In a preferred embodiment, differentiation is to a cell of the sympathoadrenal lineage or the cholinergic lineage. In another embodiment, differentiation is to a sensory neuron. In another aspect, differentiation is to a phenotype which produces dopamine and norepinephrine. In yet another aspect, differentiation is to adrenal chromaffin cells, small intensely fluorescent cells or sympathetic neurons.

The neural crest stem cell can be a single isolated cell. Moreover, the neural crest stem cell can be from a primary source or culture.

The methods provided can be applied in a number of ways including storing and forming cells which can be used in transplantation into subjects. Subjects can be individuals suffering from neurodegenerative diseases or disorders or animal models of the same.

In a further aspect, a method of culturing at least one undifferentiated cell to form a cell which produces dopamine and norepinephrine is provided. In one embodiment, the method comprises culturing said cell(s) in low ambient oxygen conditions to form a cell which produces dopamine and norepinephrine.

Other features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1 shows cells indicating low oxygen promotes sympathoadrenal lineage differentiation. Sciatic nerve p75$^+$ P$_0^-$ cells (Morrison, et al., 1999) were cultured in low oxygen or in ambient oxygen. Cultures were grown for a total of 12 days, either under standard conditions or with 5 $\mu$M forskolin and 1 ng/mL BMP2 added after 6 days of standard culture. Cultures were fixed and stained with antibodies against tyrosine hydroxylase (TH) (rate limiting enzyme for dopamine production), dopamine-$\beta$-hydroxylase (DBH), and the sympathoadrenal lineage marker SA-1. The bars show the percentage of stem cell colonies that contained cells expressing the given markers. Error bars show standard errors. Sympathetic markers were expressed at a significantly higher frequency at low oxygen and in the presence of forskolin and BMP2 ($p<0.05$).

FIGS. 2A–E show cells indicating the induction of TH expression by low oxygen culture in BMP2 plus forskolin. FIGS. 2A, 2C, and 2E are epifluorescence illumination of anti-TH antibody staining of the phase contrast fields shown in FIGS. 2B, 2D and 2F, respectively. FIGS. 2A and 2B show a colony grown in low oxygen plus 1 ng/ml BMP2 plus 5 $\mu$M forskolin. FIGS. 2C and 2E show a colony grown in low oxygen without added factors. FIGS. 2E and 2F show a colony grown in ambient oxygen plus BMP2 plus forskolin. No TH expression was seen in cultures grown in 20% oxygen without BMP2 or forskolin in this experiment. In general, only rare $TH^+$ cells were observed in ambient oxygen cultures. All figures, 10x objective magnification.

FIGS. 3A–3F show cells indicating co-expression of SA lineage markers. All figures are from cultures grown in low oxygen plus 1 ng/ml BMP2 plus 5 $\mu$M forskolin. Cultures were double-labeled with anti-TH (FIGS. 3A and 3B) and anti-DBH (FIG. 3C) or anti-SA1 (FIG. 3D). FIGS. 3E and 3F show the merged images in FIGS. 3A, 3C and FIGS. 3B, 3D, respectively. Thus, FIGS. 3A, 3C, and 3E represent the same field of one colony while FIGS. 3B, 3D, and 3F represent the same field of a second colony. FIGS. 3C and 3D were contrast-adjusted to subtract out background due to "bleed through" of R-PE secondary antibody (FIGS. 3A and 3B) into the FITC channel (FIGS. 3C and 3D); this underestimates the number of $DBH^+$ and $SA1^+$ cells in the field. Arrowheads in (FIGS. 3E and 3F) indicate double-labeled cells. All figures, 40x objective magnification.

FIGS. 4A–4F show cells indicating neuronal differentiation of SA lineage cells. Middle neurofilament (NFM; green) and tyrosine hydroxylase (TH; red) staining of stem cell colonies cultured from $p75^+P_0^-$ cells in low oxygen are shown. FIGS. 4A–4C show the same field of a single colony photographed with a 40x objective. FIGS. 4D to 4F show one field of a different colony photographed with a 20x objective. FIGS. 4B and 4E show tyrosine hydroxylase staining; FIGS. 4C and 4F show NFM staining; Figures A and D show superimpositions of the NFM and TH staining. Arrow points indicate SIF-like cells with polygonal morphology, short or absent neurites, high levels of TH staining, and low levels of NFM staining. Arrow heads indicate other SIF-like cells with polygonal morphology, long neurites, high levels of TH staining, and high NFM staining. These cells appear transitional between SIF-like cells and sympathetic neurons. Arrows indicate cells that look like sympathetic neurons, with rounded cell bodies, long neurites, moderate TH staining, and high NFM staining.

FIGS. 5A–5D show cells indicating Vesicular Acetylcholine Transporter (VAChT) expression by neurons in NCSC colonies. NCSC colonies cultured under standard conditions were stained with a polyclonal goat anti-VAChT antibody (Chemicon) followed by immunoperoxidase detection with an anti-goat second stage antibody (FIGS. 5A and 5B). Control dishes were stained only with the second stage antibody (FIGS. 5C and 5D). Although no staining was observed in response to the second stage control, colonies stained with the anti-VAChT antibody exhibited vesicular staining in most neurons. FIGS. 5A and 5C show bright field images while FIGS. 5B and 5D show phase contrast images of the same fields. All figures, 40x objective magnification.

DETAILED DESCRIPTION OF THE INVENTION

In order for cell transplantation therapies to become widely and universally used there is a need for availability of appropriately differentiated, viable cells. Preferably, these cells need to be resilient enough that they can be cryopreserved without loss of phenotypic integrity. The high incubator $O_2$ levels in which the cells are grown at ambient air $O_2$ levels (referred to herein as traditional $O_2$ conditions; or 20% $O_2$ culture conditions) do not facilitate the production of such cells. As such expansion of these cells in traditional culture yields a cell that is at best inadequate for use in an in vitro model assay let alone for use in transplantation.

The present invention is directed towards providing methods and compositions for producing cells that are differentiated, viable, amenable to cryopreservation and provide an accurate indication of how such cells behave biochemically in an in vivo setting. As such, these methods will provide cells that can be used in vitro to perform characterization studies or in vivo as replacement therapies for cells that have been damaged by disease, injury resulting from trauma, ischemia, or a drug-induced injury.

In one aspect of the invention, a method of culturing at least one neural crest stem cell (NCSC) to enhance survival, proliferation or differentiation of the NCSC is provided. In a preferred embodiment, the method comprises culturing at least one NCSC in low ambient oxygen conditions, wherein the survival, proliferation or differentiation is enhanced compared to a control NCSC cultured in ambient oxygen conditions.

As used herein, the term "neural crest stem cell" means a cell derived from the neural crest which is characterized by having the properties (1) of self-renewal and (2) asymmetrical division; that is, one cell divides to produce two different daughter cells with one being self (renewal) and the other being a cell having a more restricted developmental potential, as compared to the parental neural crest stem cell. The foregoing, however, is not to be construed to mean that each cell division of a neural crest stem cell gives rise to an asymmetrical division. It is possible that a division of a neural crest stem cell can result only in self-renewal, in the production of more developmentally restricted progeny only, or in the production of a self-renewed stem cell and a cell having restricted developmental potential. The neural crest gives rise to the peripheral nervous system (PNS).

Regarding any methods provided herein, a single cell or cells at clonal density are preferred. As used herein, the term "clonal density" means a density sufficiently low enough to result in the isolation of single, non-impinging cells when plated in a culture dish, generally about 225 cells/100 mm culture dish. Furthermore, the cells can be primary or from cultures, adult or fetal origin. Moreover, while human cells are preferred, any mammalian cell can be used in this invention, including cells from mice, cattle, sheep, goat, pigs, dogs, rats, rabbits, and primates.

The phrase "low ambient oxygen conditions" as used herein refers to any culturing conditions below atmospheric oxygen. Moreover, the phrase is sometimes used interchangeably herein with "subatmospheric" or "low oxygen" conditions. Low ambient oxygen conditions generally means any oxygen concentration below about 20%, preferably below about 15%, more preferably below about 10%, at sea level. Preferably, the culture oxygen conditions are kept as close as possible to the normal physiological oxygen conditions in which a particular cell would be found in vivo. Thus, in some embodiments, the conditions employed for cells will depend on the regional origin of a particular cell; such conditions are known to the skilled artisan. "Physiologic" oxygen levels are the range of oxygen levels normally found in healthy tissues and organs.

In one embodiment, the low ambient oxygen conditions comprise an ambient oxygen condition of between about 0.25% to about 18% oxygen. In another embodiment, the ambient oxygen conditions comprise an ambient oxygen condition of between about 0.5% to about 15% oxygen. In still another embodiment, the low ambient oxygen conditions comprise an ambient oxygen condition of between about 1% to about 10% oxygen. In further embodiments, the low ambient oxygen conditions comprise an ambient oxygen condition of between about 1.5% to about 6% oxygen. Of course, these are exemplary ranges of ambient oxygen conditions to be used in culture and it should be understood that those of skill in the art will be able to employ oxygen conditions falling in any of these ranges generally or oxygen conditions between any of these ranges that mimics physiological oxygen conditions for the particular cells. Thus, one of skill in the art could set the oxygen culture conditions at 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, or any other oxygen condition between any of these figures.

It should be noted that the low ambient oxygen conditions are not to be considered the same as "hypoxic" conditions. The low ambient oxygen conditions are intended to mimic physiological conditions. As defined herein "hypoxic conditions" are those in which the oxygen level is less than 0.1% $O_2$. Hypoxia occurs when the normal physiologic levels of oxygen are not supplied to a cell or tissue. Hypoxic conditions are those leading to cellular hypoxia.

In one aspect, the methods provided herein are to enhance survival, proliferation or differentiation of a cell. The term "enhance" as used herein means any increase over a control cell in ambient or atmospheric oxygen conditions. "Atmospheric $O_2$ conditions" are those conditions found in the air, i.e., 20–21% $O_2$. As used herein this term is used interchangeably with the term "traditional" $O_2$ conditions as traditional tissue culture incubators are kept at atmospheric $O_2$ conditions.

In one aspect, survival is enhanced. "Survival" as used herein may include a delay or decreased rate in either apoptotic and non-apoptotic cell death. Any enhancement of survival of a cell provides a number of uses. For example, survival provides facilitation to handle tissue before administration of cell therapy or any other procedure during which the cells must survive such as transfection of genes, drug treatment, or enrichment by cell sorting or other additional procedures. In a preferred embodiment, survival is increased at least 10%, more preferably at least 20% and most preferably at least 30%. For example, in a preferred embodiment, if about 35% of cells added to culture form colonies in ambient oxygen, then about 48% of cells form colonies in low ambient conditions. Other preferred embodiments include enhancement of at least 50% or 75% to 100% or 2× or 3× the survival rate.

In another embodiment herein, neural crest stem cells are more likely to form multilineage colonies in low oxygen. Preferably, the low oxygen conditions produce at least a 10% or 20% increase, more preferably, a 30% to 40% increase, and more preferably, at least a 50% to 60% increase. For example, if in ambient oxygen only 48% of colonies are multilineage (containing neurons, Schwann cells, and myofibroblasts), with the balance being Schwann cells, then low oxygen conditions will produce colonies which are at least 80% multipotent.

In yet another aspect herein, proliferation is enhanced. "Proliferation" refers to an increase in the number of cells in a population (growth) by means of cell division. Cell proliferation is generally understood to result from the coordinated activation of multiple signal transduction pathways in response to the environment, including growth factors and other mitogens. Cell proliferation may also be promoted by release from the actions of intra- or extracellular signals and mechanisms that block or negatively affect cell proliferation. In a preferred embodiment, proliferation is increased at least 10% to 50%, more preferably at least 50% to 100% and more preferably, proliferation is 2 to 3×, or 4× to 5×. Most preferably, cells in low (also called decreased) oxygen form colonies containing about twice as many cells as those grown in ambient conditions.

In a further aspect of the invention, differentiation is enhanced. "Differentiation" refers to the developmental process whereby cells assume a specialized phenotype, i.e., acquire one or more characteristics or functions distinct from other cell types. In most uses, the differentiated phenotype refers to a cell phenotype that is at the mature endpoint in some developmental pathway. In many but not all tissues, the process of differentiation is coupled with exit from the cell cycle; in these cases, the cells lose or greatly restrict their capacity to proliferate when they differentiate. Thus, in one embodiment, low oxygen conditions promote a higher proportion of colonies that contain only neurons and a lower proportion that contain no neurons compared to ambient oxygen conditions. In a preferred embodiment, if one third of colonies in ambient oxygen conditions have all neurons, two thirds of colonies in low ambient oxygen conditions have all neurons. In other embodiments, the proportion of colonies having all neurons is increased 25% to 50%, more preferably, 50% to 100%, more preferably, 150% to 200% and more preferably, 300% or 400%.

In another embodiment, if about one sixth of colonies in ambient oxygen conditions have no neurons, about a twentieth of colonies in low ambient oxygen conditions have no neurons. In other embodiments, the proportion of colonies having no neurons is increased at least 25% to 50%, more preferably, 50% to 100%, more preferably, 150% to 200%, and more preferably, 200% to 300% or 400%.

In one aspect of the invention, differentiation is to a particular phenotype. Preferred phenotypes include cells that express one or more of tyrosine hydroxylase, dopamine beta hydroxlase and the sympathoadrenal lineage specific antigen SA-1. In another embodiment, the cells are differentiated to become PNS sensory cells, sympathoadrenal cells or cholinergic cells. In preferred embodiments, the method can be used to produce dopaminergic or noradrenergic cells.

In one aspect, wherein a particular phenotype is formed, a variety of cells may be used. In a preferred embodiment, the differentiated cell produces both dopamine and norepinephrine. In one embodiment, a progenitor or a stem cell is utilized. A "stem cell" is a relatively undifferentiated cell that can be induced to proliferate and that can produce progeny that subsequently differentiate into one or more mature cell types, while also retaining one or more cells with parental developmental potential. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype.

"Progenitor cells" have a cellular phenotype that is more primitive (i.e., is at an earlier step along a developmental pathway or progression than is a fully differentiated cell). Often, progenitor cells also have significant or very high proliferative potential. Progenitor cells may give rise to multiple distinct differentiated cell types or to a single differentiated cell type, depending on the developmental pathway and on the environment in which the cells develop and differentiate. Like stem cells, it is possible that cells that begin as progenitor cells might proceed toward a differentiated phenotype, but then "reverse" and re-express the progenitor cell phenotype.

In one aspect, the present invention is used to generate viable cells or tissue that can be used to ameliorate neurodegenerative disorders. Such cells or tissue upon transplantation can be referred to as a graft. The cells for transplantation can include but are not limited to human or animal neurons for stroke, brain and spinal cord injury, Alzheimer's disease, Parkinson's disease and other neurodegenerative disorders. For example, the hallmark of Alzheimer's disease is the loss of cholinergic cells, whereas Parkinson's patients suffer from the loss of dopaminergic cells. Such cells can be efficiently formed by in vitro the methods herein.

In regards to forming the cells herein, in one aspect, subatmospheric culturing conditions can be used from the start of cell isolation, in order to enrich the cell pool and enhance differentiation into a greater number of cells. "Enriching" of cells means that the yield (fraction) of cells of one type is increased over the fraction of cells in the starting culture or preparation. Subatmospheric/physiologic culture conditions can also be used after initial plating and division, to up-regulate certain gene products in the more differentiated cells. Subatmospheric/physiologic culture conditions can also be used throughout the process to enhance the function of the entire population for transplantation or other use.

Suitable medium and conditions for generating primary cultures are well known in the art and vary depending on cell type. As a general principle, when the goal of culturing is to keep cells dividing, serum is added to the medium in relatively large quantities (10–20% by volume). Specific purified growth factors or cocktails of multiple growth factors can also be added or sometimes used in lieu of serum. As a general principle, when the goal of culturing is to reinforce differentiation, serum with its mitogens is generally limited (serum about 1–2% by volume). Specific factors or hormones that promote differentiation and/or promote cell-cycle arrest can also be used.

Physiologic oxygen and subatmospheric oxygen conditions can be used at any time during the growth and differentiation of cells in culture, as a critical adjunct to selection of specific cell phenotypes, growth and proliferation of specific cell types, or differentiation of specific cell types. In general, physiologic or low oxygen-level culturing is accompanied by methods that limit acidosis of the cultures, such as addition of strong buffer to medium (such as Hepes), and frequent medium changes and changes in $CO_2$ concentration. "Acidosis" means that the pH is below normal physiologic levels.

Cells can be exposed to the low oxygen conditions in a variety of ways. Specialized laboratory facilities may have completely enclosed environments in which the oxygen levels are controlled throughout a dedicated, isolated room. In such specialized areas, low oxygen levels can be maintained throughout the isolation, growth and differentiation of cells without interruption. Physiologic or low oxygen culturing conditions also can be maintained by using commercially-available chambers which are flushed with a pre-determined gas mixture (e.g., as available from Billups-Rothenberg, San Diego, Calif.). As an adjunct, medium can be flushed with the same gas mixture prior to cell feeding. In general, it is not possible to maintain physiologic or low oxygen conditions during cell feeding and passaging using these smaller enclosed units, and so, the time for these manipulations should be minimized as much as possible. Any sealed unit can be used for physiologic oxygen or low oxygen level culturing provided that adequate humidification, temperature, and carbon dioxide are provided.

In addition to oxygen, the other gases for culture typically are about 5% carbon dioxide and the remainder is nitrogen, but optionally may contain varying amounts of nitric oxide (starting as low as 3 ppm), carbon monoxide and other gases, both inert and biologically active. Carbon dioxide concentrations typically range around 5% as noted above, but may vary between 2–10%. Both nitric oxide and carbon monoxide are typically administered in very small amounts (i.e. in the ppm range), determined empirically or from the literature.

The cells are typically exposed to low oxygen level conditions for a time sufficient to enrich the population of progenitor/stem cells compared to other cell types. Typically this is for 1 or more hours, preferably 3 or more hours, more preferably 6 or more hours, and most preferably 12 or more hours, and may be continuous. The temperature during the culture is typically reflective of core body temperature, or about 37° C., but may vary between about 32° C. and about 40° C.

Following an initial exposure to low or physiologic oxygen culturing conditions, cells can be maintained in these conditions or returned to normal laboratory oxygen conditions, depending on the desired outcome.

The cells can be used in a variety of applications. The physiologic/subatmospheric culturing conditions described herein can be used to differentiate specific populations of cells useful for transplantation, and to expand the number of available cells derived from a variety of culture systems.

Methods of grafting cells are now well known to those of skill in art (U.S. Pat. No. 5,762,926; U.S. Pat. No. 5,650,148; U.S. Pat. No. 5,082,670). Neural transplantation or grafting involves transplantation of cells into the central nervous system or into the ventricular cavities or subdurally onto the surface of a host brain. Conditions for successful transplantation include: 1) viability of the implant; 2) retention of the graft at the site of transplantation; and 3) minimum amount of pathological reaction at the site of transplantation. The cells can be from the patient (autologous) or from a foreign individual (same or different species, preferably same).

Methods for transplanting various nerve tissues, for example embryonic brain tissue, into host brains have been described in Neural Grafting in the Mammalian CNS, Bjorklund and Stenevi, eds., (1985) Das, Ch. 3 pp. 23–30; Freed, Ch. 4, pp. 31–40; Stenevi et al., Ch. 5, pp. 41–50; Brundin et al., Ch. 6, pp. 51–60; David et al., Ch. 7, pp. 61–70; Seiger, Ch. 8, pp. 71–77 (1985), incorporated by reference herein. These procedures include intraparenchymal transplantation, i.e. within the host brain (as compared to outside the brain or extraparenchymal transplantation) achieved by injection or deposition of tissue within the host brain so as to be opposed to the brain parenchyma at the time of transplantation (Das, supra).

The two main procedures for intraparenchymal transplantation are: 1) injecting the donor cells within the host brain parenchyma or 2) preparing a cavity by surgical means to expose the host brain parenchyma and then depositing the graft into the cavity (Das, supra). Both methods provide parenchymal apposition between the graft and host brain tissue at the time of grafting, and both facilitate anatomical integration between the graft and host brain tissue. This is of importance if it is required that the graft become an integral part of the host brain and to survive for the life of the host.

Alternatively, the graft may be placed in a ventricle, e.g. a cerebral ventricle or subdurally, i.e. on the surface of the host brain where it is separated from the host brain parenchyma by the intervening pia mater or arachnoid and pia mater. Grafting to the ventricle may be accomplished by injection of the donor cells or by growing the cells in a substrate such as 3% collagen to form a plug of solid tissue which may then be implanted into the ventricle to prevent dislocation of the graft. For subdural grafting, the cells may be injected around the surface of the brain after making a slit in the dura. Injections into selected regions of the host brain may be made by drilling a hole and piercing the dura to permit the needle of a microsyringe to be inserted. The microsyringe is preferably mounted in a stereotaxic frame and three dimensional stereotaxic coordinates are selected for placing the needle into the desired location of the brain or spinal cord.

The donor cells may also be introduced into the putamen, nucleus basalis, hippocampus cortex, striatum or caudate regions of the brain, as well as the spinal cord.

For grafting, the cell suspension is drawn up into the syringe and administered to anesthetized graft recipients. Multiple injections may be made using this procedure. The age of the donor tissue, i.e., the developmental stage, may affect the success of cell survival after grafting.

The cellular suspension procedure thus permits grafting of donor cells to any predetermined site in the brain or spinal cord, is relatively non-traumatic, allows multiple grafting simultaneously in several different sites or the same site using the same cell suspension, and permits mixtures of cells from different anatomical regions. Multiple grafts may consist of a mixture of cell types, and/or a mixture of transgenes inserted into the cells. Preferably from approximately $10^4$ to approximately $10^8$ cells are introduced per graft.

For transplantation into cavities, which may be preferred for spinal cord grafting, tissue is removed from regions close to the external surface of the CNS to form a transplantation cavity, for example by removing bone overlying the brain and stopping bleeding with a material such a gelfoam (Stenevi et al., Brain Res. 114:1–20 (1976)). Suction may be used to create the cavity. The graft is then placed in the cavity. More than one transplant may be placed in the same cavity using injection of cells or solid tissue implants.

Grafting of donor cells into a traumatized brain will require different procedures, for example, the site of injury must be cleaned and bleeding stopped before attempting to graft. In addition, the donor cells should possess sufficient growth potential to fill any lesion or cavity in the host brain to prevent isolation of the graft in the pathological environment of the traumatized brain.

In one embodiment, the cells generated by the methods herein are used on an animal model of a disease. For example, a rat model of Parkinson's disease can be created by giving a unilateral injection of saline-ascorbate 6-hydroxy-dopamine (6-OHDA) into the medial forebrain bundle. This produces a lesion that ultimately mimics Parkinsonian behavior. Completeness of the lesion produced can by monitoring either apomorphine or amphetamine induced rotational behavior. Animals turning at a rate of more than 7 turns per minute can be inferred to have the appropriate lesion (at least 7 contralateral rotations/min following apomorphine administration and at least 7 ipsilateral rotations/min towards the side of the lesion following amphetamine administration).

Using such a model a baseline rotation behavior can be established. After that, the cells grown in the present invention can then be transplanted into the rat model as described herein above. Any decrease in the rotational behavior would be indicative of the cellular transplant having an appropriate therapeutic value. Similarly, other animal models are known in the art and can be used in conjunction with the methods herein.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

METHODS

Isolation of sciatic nerve $p75^+P_0$-

Pregnant Sprague-Dawley rats were obtained from Simonsen (Gilroy, Calif.). For timed pregnancies, animals were put together in the afternoon and the morning on which the plug was observed was designated E0.5. Neural crest stem cells were isolated from E14.5 sciatic nerves as described previously (Morrison, et al., 1999). Briefly, nerves were dissected and dissociated by incubating in trypsin plus collagenase for 4 minutes at 37° C. followed by mechanical trituration. The cells were stained with monoclonal antibodies against p75 (192Ig), the low-affinity neurotrophin receptor, and $P_0$ (P07), a PNS myelin component. All sorts and analyses were performed on a FACSVantage flow-cytometer (Becton-Dickinson, San Jose). NCSCs were sorted as live $p75^+P_0$- cells.

Culture conditions

Sciatic nerve progenitors were cultured at clonal density as described previously (Morrison et al., 1999). Briefly, plates were coated with poly-d-lysine (Biomedical Technologies, Stoughton, Mass.) and human fibronectin (Biomedical Technologies). The culture medium contained DMEM-low glucose (Gibco) with 15% chick embryo extract (Stemple, et al., 1992), 20 ng/ml recombinant human bFGF (R&D Systems, Minneapolis), N2 supplement (Gibco), B27 supplement (Gibco), 50 µM 2-mercaptoethanol, 35 mg/ml retinoic acid (Sigma), and penicillin/streptomycin (BioWhittaker). This composition is described throughout as "standard medium". Under standard conditions, cells were cultured for 6 days in standard medium, then switched to a similar medium (with 1% CEE and 10 ng/ml bFGF) that favors differentiation for another 8 days before immunohistochemical analysis of colony composition. To promote sympathetic differentiation, 5 µM forskolin and 1 ng/ml BMP2 (Genetics Institute) were sometimes added after the first 6 days of standard culture, and the cultures were allowed to develop for another 6 days. To further promote sympathetic neuron differentiation the cultures were switched to standard medium containing 50 ng/ml NGF and 50 ng/ml NT3 for a final 6 days.

Normal humidified tissue culture incubators with around 6% $CO_2$ were used for 20% oxygen cultures. For decreased oxygen cultures, plates were inserted into gas-tight modular incubator chambers (Billups-Rothenberg, Del Mar, Calif.) that were flushed with a custom gas mixture containing 1% $O_2$/6% $CO_2$/balance $N_2$. The incubator chambers were flushed for one and a half to two minutes daily at a rate of 15 liters per minute, then inserted into normal tissue culture incubators. This achieved an actual concentration inside the chamber of around 5% oxygen, based on direct measurement with a microelectrode (Animus Corp., Malvern, Pa.). Although 5% oxygen is commonly described as hypoxic relative to atmospheric oxygen, it actually generates a tissue culture environment closer to physiological levels (Guyton, et al., 1996).

Immunohistochemistry

For routine analysis of culture compositions, cultures were fixed in acid ethanol and stained with antibodies against peripherin (Chemicon AB1530, Temecula, Calif.), smooth muscle actin (Sigma A-2547), and GFAP (Sigma G-3893) as described previously (Morrison, et al., 1999). In order to stain for sympathetic markers, cultures were fixed in 4% paraformaldehyde, blocked in PBS with 4% goat serum plus 0.2% BSA plus 0.1% NP-40, then stained with antibodies against tyrosine hydroxylase (Boehringer Mannheim, Indianapolis, Ind.), and/or dopamine-beta-hydroxylase (Pharmingen, San Diego, Calif.), or SA-1 (a gift of Paul Patterson). VAChT staining was performed on 4% paraformaldehyde fixed cultures, blocked in horse serum, and stained for an hour at room temperature in goat polyclonal antibody (Chemicon AAB1578), followed by immunoperoxidase detection (nickel/diaminobenzidine precipitation).

HPLC Analysis of Dopamine and Norepinephrine

A Shimadzu solvent delivery system was used with the following mobile phase: 92% 75 mM $NaH_2PO_4$, 1.7 mM octanesulfonic acid, 0.05 mM EDTA, pH 3.1; 8% acetonitrile, at a flow rate of 0.8 ml/min. An Alltech Absorbosphere HS C18 reverse phase column (10×4.6 mm, 3 µm) was connected to an electrochemical detector (ESA: Coulochem II) set at an applied potential of +0.02V at detector 1 and +0.40V at detector 2. Detector response was linear for 0.05–10 ng (r=0.99 for linear regression calculations of all compounds assayed; within-assay variance was less than 5%). Peak areas were quantitated with a Rainin MACintegrator system. No DA or NE were detected in blank samples prepared from solvent, or from a control colony cultured under standard conditions in 20% oxygen.

Decreased oxygen culture promotes the survival, proliferation, and neuronal differentiation of NCSCs NCSCs were isolated by flow-cytometry from the sciatic nerves of E14.5 rats and sorted into culture at clonal density under standard conditions (Morrison, et al., 1999). Some cultures were kept in normal incubators containing 6% $CO_2$ and 20% $O_2$ (from air), while other cultures were kept in gas-tight chambers that were flushed with 1% $O_2$/6% $CO_2$/balance $N_2$ to generate an actual $O_2$ level of 5%. After 15 days the plates were stained with antibodies against peripherin (to detect neurons), glial fibrillary acidic protein (GFAP; to detect glia), and smooth muscle actin (SMA; to detect myofibroblasts). The results are presented in Table 1. The ability of $p75^+P_0$- cells to survive and form colonies was significantly greater in decreased oxygen: 35% of cells added to culture formed colonies in 20% oxygen versus 48% of cells in 5% oxygen (p<0.01).

TABLE 1

Culture of sciatic nerve $p75^+P_0$-cells in decreased oxygen promotes neural crest stem cell survival and multilineage differentiation

| | Plating efficiency (%) | frequency of colony types (%) | | | | |
|---|---|---|---|---|---|---|
| | | N + S + M | N + S | S + M | S only | M only |
| 20% $O_2$ | 35.0 ± 9.1 | 48.0 ± 16.4 | 1.0 ± 2.1 | 4.8 ± 3.4 | 43.7 ± 18.5 | 2.5 ± 3.0 |
| 5% $O_2$ | 48.0 ± 5.8* | 82.8 ± 12.0* | 0.4 ± 1.0 | 8.1 ± 7.4 | 6.2 ± 3.6* | 2.5 ± 3.1 |

$p75^+P_0$- cells were sorted into culture at clonal density and cultured for 15 days followed by immunohistochemistry. Plating efficiency indicates the percentage of cells sorted into culture that went on to form colonies detected 15 days later. N, S, and M mean that neurons, Schwann cells, and myofibroblasts respectively were observed within colonies. For example, N+S+M colonies contained neurons, Schwann cells and myofibroblasts. Data are presented as mean±standard deviation and were derived from 6 independent experiments in which an average of more than 70 colonies were counted per treatment per experiment. Results were compared by t tests and significantly different statistics are noted by * (P<0.05).

In addition to improved survival, $p75^+P_0$- cells were more likely to form multilineage colonies in 5% oxygen. In 20% oxygen only 48% of colonies were multilineage (containing neurons, Schwann cells, and myofibroblasts; N+S+M in Table 1), with the balance being mainly Schwann-only colonies (S-only, Table 1). In contrast, in 5% oxygen cultures significantly more colonies were multipotent (82%) and significantly fewer colonies were Schwann-only (6%). One possible explanation for this difference is that more than 80% of $p75^+P_0$- cells are multipotent but that multipotent progenitors sometimes give rise only to Schwann cells when cultured in 20% oxygen. The other possibility is that decreased oxygen levels are toxic to glial-committed progenitors such that their frequency is underestimated. The significantly higher plating efficiency in decreased oxygen argues against the latter possibility. Nonetheless this was tested by culturing E18.5 sciatic nerve cells in standard medium in either 5% or 20% oxygen. Multipotent progenitors have not been detected in the sciatic nerve after E17.5, so most or all neural progenitors in the E18.5 nerve appear to be glial committed (Morrison, et al., 1999; Jessen, et al., 1999). The frequencies of Schwann-only or myofibroblast-only colonies did not differ between 5% and 20% oxygen cultures: 23% of E18.5 sciatic nerve cells formed Schwann-only colonies, and 22% formed myofibroblast-only colonies irrespective of oxygen level (the remaining 55% of cells died without forming colonies). Consistent with this, decreased oxygen did not affect the overall plating efficiency in mass cultures of E14.5 sciatic nerve cells, of which NCSCs constituted only 15–20% (data not shown). These data support the idea that decreased oxygen culture promotes the survival and multilineage differentiation of NCSCs, without biasing against the survival of more restricted progenitors. The $p75^+P_0$- population appears to contain more than 80% NCSCs.

To test whether $p75^+P_0$- cells self-renew in decreased oxygen culture a single cell was deposited per well of a 96 well plate then seven colonies were subcloned after 7 days. All founder clones gave rise to multipotent subclones, averaging 158±149 multipotent subclones per founder, demonstrating that individual $p75^+P_0$- cells self-renew in decreased oxygen as was previously documented in 20% oxygen (Morrison, et al., 1999).

Decreased oxygen culture also promoted the proliferation of NCSCs. As described previously (Morrison, et al., 1999), multipotent colonies can be distinguished from other colony types based on their appearance. After 6 days of culture colonies predicted to be multipotent contained 289±237 cells in 20% oxygen (n=9) or 589±156 cells in 5% oxygen (n=6). This difference in colony size (p=0.018) must have been due to a difference in proliferation since after only 6 days of culture few dead cells were observed in the colonies at either oxygen level: 7.1±5.6 cells per colony in 20% oxygen or 17.5±7.0 cells per colony in 5% oxygen appeared dead by morphology. Thus in decreased oxygen NCSC clones proliferated to a significantly greater extent forming colonies that contained around twice as many cells by the sixth day of culture.

Under standard culture conditions neurons are almost never observed in colonies that do not also contain Schwann cells and myofibroblasts (Table 1; (Morrison, et al., 1999). Thus neuronal potential is associated with NCSC activity. BMP2 instructs NCSCs to differentiate into neurons (Shah, et al., 1996; Morrison, et al., 1999). As an independent test of neuronal potential we added BMP2 to cultures of $p75^+P_0$- cells in either 5% or 20% oxygen. After 4 to 6 days, the cultures were stained for peripherin to analyze the extent of neuronal differentiation. The results are shown in Table 2.

on to form colonies. Data are presented as mean±standard deviation for 5 independent experiments. Results at different oxygen concentrations (within no add or +BMP2 treatments) were compared by t tests and significantly different statistics are noted by * ($P<0.05$). Decreased oxygen culture significantly increased plating efficiency in both treatments and neuronal differentiation in the presence of BMP2.

As seen previously, a higher proportion of $p75^+P_0$- cells survived and formed colonies in decreased oxygen, irrespective of whether BMP2 was added. Almost no colonies contained peripherin$^+$ cells in the cultures that did not receive BMP2 (peripherin expression is normally not evident for at least 12 days under standard culture conditions). However, among cultures to which BMP2 was added, decreased oxygen was associated with a significantly higher proportion of colonies that contained only neurons and a significantly lower proportion of colonies that contained no neurons. In decreased oxygen nearly 60% of colonies contained only neurons and almost 95% of colonies contained at least some neurons. Thus neuronal differentiation was significantly promoted in decreased oxygen culture and up to 95% of $p75^+P_0$- cells may be NCSCs.

Decreased oxygen culture reveals that virtually all NCSCs isolated from sciatic nerve have SA lineage potential $p75^+P_0$- cells were added to culture at clonal density in standard conditions in either 5% of 20% oxygen. After 6 days of culture, 5 $\mu$M forskolin and 1 ng/ml BMP2 were added to some cultures. Following a total of 12 days in culture, colonies were stained for three markers of sympathetic lineage differentiation: TH, DBH, and SA-1 a marker of chromaffin cells and sympathoadrenal progenitors (Carnahan, et al., 1991). In both standard cultures and cultures supplemented with forskolin and BMP2, decreased oxygen significantly increased the proportion of colonies that contained cells expressing TH, DBH, or SA-1 (FIG. 1). In decreased oxygen cultures supplemented with forskolin and BMP2 nearly all stem cell colonies contained TH$^+$ cells, DBH$^+$ cells and SA-1$^+$ cells (FIG. 1). In addition to increasing the proportion of colonies expressing sympathetic markers, decreased oxygen and/or the addition of forskolin and BMP2 also tended to increase the proportion of cells within colonies expressing the markers and the intensity of marker expression (FIG. 2).

In cultures grown in BMP2 plus forskolin in 5% $O_2$, cells often co-expressed TH and DBH, or TH and SA-1. In colonies double stained for TH and DBH, many TH$^+$ cells were also DBH$^+$ (and vice versa) though there were also subsets of TH$^+$DBH$^-$ and TH$^-$DBH$^+$ cells (FIG. 3). In

TABLE 2

BMP2 instructed neuronal differentiation of sciatic nerve $p75^-P_0$-cells is promoted by culture in decreased oxygen.

|  |  | Plating efficiency (%) | types of colonies (%) | | |
|---|---|---|---|---|---|
|  |  |  | all neurons | some neurons | no neurons |
| no add | 20% $O_2$ | 22.7 ± 8.5 | 0.0 ± 0.0 | 0.0 ± 0.0 | 100.0 ± 0.0 |
|  | 5% $O_2$ | 33.4 ± 7.3* | 0.0 ± 0.0 | 0.4 ± 0.9 | 99.6 ± 0.9 |
| +BMP2 | 20% $O_2$ | 26.8 ± 8.9 | 31.5 ± 17.9 | 52.5 ± 18.9 | 15.9 ± 5.7 |
|  | 5% $O_2$ | 43.4 ± 11.5* | 59.5 ± 10.8* | 35.0 ± 11.1 | 5.5 ± 1.4* |

$p75^+P_0$- cells were sorted into cultures at clonal density and cultured for 5 or 6 days followed by staining for peripherin, a marker of peripheral neurons. Plating efficiency indicates the percentage of cells initially sorted into culture that went colonies double labeled for TH and SA-1, all or nearly all SA-1$^+$ cells were TH$^+$ and many TH$^+$ cells were also SA-1$^+$, but some were SA-1$^-$ (FIG. 3). Because the antibodies against SA-1 and DBH are of the same isotype it was not possible to double stain for those markers. These data demonstrate that virtually all NCSCs isolated from E14.5 sciatic nerve and cultured under these conditions have SA lineage potential.

TH+ cells derived from NCSCs co-express neuronal markers and release dopamine and norepinephrine To promote overt neuronal differentiation by these cells, we cultured $p75^+P_0^-$ cells in decreased oxygen at clonal density for 6 days in standard medium, followed by 6 days supplemented with forskolin and low BMP2, followed by a final 6 days supplemented by 50 ng/ml each of NGF and NT-3 (which have been shown to promote the differentiation and survival of sympathetic neuroblasts in vitro (Birren, et al., 1993; Verdi, et al., 1994). Under these conditions, 3.6±2.5% of cells in each colony were TH+. These stem cell colonies contain more than $10^5$ cells (Morrison, et al., 1999), so individual $p75^+P_0^-$ cells gave rise to thousands of SA-lineage cells.

Double-labeling of cultures grown under these conditions with antibodies to TH and neurofilament middle molecular weight subunit (NFM) revealed that the colonies contained three TH+ cell types that were distinct with respect to morphology and NFM staining. One type displayed a polygonal morphology with small or absent neurites, very strong TH staining, and low NFM staining (FIGS. 4A, B, arrow points), resembling SIF or chromaffin-like cells (Doupe, et al., 1985) and references therein). There were also polygonal cells with longer varicose processes that had very strong TH staining and intermediate levels of NFM staining (FIGS. 4B, E, arrowheads), appearing intermediate in phenotype between SIF cells and sympathetic neurons. Finally, other cells had round cell bodies, long neurites, a lower level of TH staining, and strong NFM staining, resembling immature sympathetic neurons (FIG. 4, arrows). Of 29 NCSC colonies cultured under neuron-promoting conditions and then double labeled for TH and NFM, all contained cells resembling SIF cells and sympathetic neurons.

In preliminary experiments, we used HPLC analysis to determine whether colonies derived from individual NCSCs that contained TH+ and DBH+ cells also produced both DA and NE. Single $p75^+P_0^-$ cells were sorted into individual wells of 96 well plates and then cultured under sympathetic neuron-promoting conditions. Some colonies were trypsinized, resuspended in 0.2M perchloric acid, and analyzed for DA and NE content by HPLC. DA and NE peaks were identified by retention times that were similar to authentic standards (<0.1 min). 3/3 colonies contained DA and 2/3 contained NE; the DA:NE molar ratio in colonies that contained both was approximately 1:1. Other colonies were depolarized by incubation for 5 minutes in 40 mM KCl in HBSS to induce transmitter release, then the supernatants and the cells were analyzed by HPLC. Five of 8 such supernatants contained DA and 6 of 8 contained NE; in three of the 5 samples containing both transmitters the ratio was close to 1:3 (DA:NE). In cells extracted after depolarization, 4/4 contained some residual DA but none contained detectable NE. These data are consistent with the fact that DA is both vesicular and cytoplasmic, whereas NE is exclusively vesicular in catecholaminergic cells.

We were interested in the neurotransmitter phenotype of the neurons generated by NCSCs that did not express SA markers. An obvious possibility is that these cells are cholinergic, given the close developmental relationship between the sympathetic and parasympathetic (cholinergic) lineages. Most of the neurons that developed in NCSC colonies grown under standard conditions were stained by a commercial polyclonal antibody to vesicular acetylcholine transporter (VAChT) (FIG. 5). Although the staining was weak and could only be detected by the immunoperoxidase method, it had the appropriate punctate vesicular localization. Attempts to perform double-labeling of cultures containing SA lineage cells with antibodies to TH and VAChT were unsuccessful due to the low level of expression of the latter antigen, although expression of VAChT in such cultures could be detected by immunoperoxidase single labeling (not shown). Nevertheless, the fact that all colonies contained VAChT+ neurons under standard conditions, while almost all colonies switched from standard conditions to BMP2 plus forskolin contained TH+ cells (FIG. 1), indicates that isolated NCSCs have both parasympathetic and SA lineage capacities.

The finding that decreased oxygen culture can promote the production of greatly expanded numbers of dopaminergic neurons from individual, purified stem cells is an important tool to facilitate transplantation into Parkinson's patients. Under our culture conditions individual NCSCs gave rise to an average of more than 3000 TH+ cells per colony. This was without any special effort to promote stem cell expansion or to optimize sympathetic differentiation. Thus, modest efforts in those regards as known to the skilled artisan could yield additional substantial increases in the numbers of dopaminergic cells. The ability to generate thousands or millions of dopaminergic cells from a single stem cell provides both a defined precursor cell and adequate dopaminergic cells for therapeutic transplantation.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference. Of note, the text of the application may say "et al." wherein all of the authors are listed below.

Doupe, A. J., Landis, S. C. & Patterson, P. H. Environmental influences in the development of neural crest derivatives: glucocorticoids, growth factors and chromaffin cell plasticity. *J. Neurosci.* 5, 2119–2142 (1985).

Doupe, A. J., Patterson, P. H. & Landis, S. C. Small intensely fluorescent (SIF) cells in culture: role of glucocorticoids and growth factors in their development and phenotypic interconversions with other neural crest derivatives. *J. Neurosci.* 5, 2143–2160 (1985).

Anderson, D. J. Molecular control of cell fate in the neural crest: the sympathoadrenal lineage. *Annu. Rev. Neurosci.* 16, 129–158 (1993).

Fraser, S. E. & Bronner-Fraser, M. E. Migrating neural crest cells in the trunk of the avian embryo are multipotent. *Development* 112, 913–920 (1991).

Stemple, D. L. & Anderson, D. J. Isolation of a stem cell for neurons and glia from the mammalian neural crest. *Cell* 71, 973–985 (1992).

Varley, J. E., Wehby, R. G., Rueger, D. C. & Maxwell, G. D. Number of adrenergic and islet-1 immunoreactive cells is increased in avian trunk neural crest cultures in the presence of human recombinant osteogenic protein-1. *Dev. Dynam.* 203, 434–447 (1995).

Varley, J. E. & Maxwell, G. D. BMP-2 and BMP-4, but not BMP-6, increase the number of adrenergic cells which develop in quail trunk neural crest cultures. *Exp. Neurol.* 140, 84–94 (1996).

Reissman, E. et al. Involvement of bone morphogenetic protein-4 and bone morphogenetic protein-7 in the differentiation of the adrenergic phenotype in developing sympathetic neurons. *Development* 122, 2079–2088 (1996).

Lo, L., Morin, X., Brunet, J.-F. & Anderson, D. J. Specification of neurotransmitter identity by Phox2 proteins in neural crest stem cells. *Neuron* 22, 693–705 (1999).

Shah, N. M., Groves, A. & Anderson, D. J. Alternative neural crest cell fates are instructively promoted by TGF superfamily members. *Cell* 85, 331–343 (1996).

Gage, F. H. & Buzs‡ki, G. CNS grafting: potential mechanisms of action. in *Neural Regeneration and Transplantation* 211–226 (Alan R. Liss, Inc., New York, 1989).

Freed, C. R. et al. Survival of implanted fetal dopamine cells and neurologic improvement 12 to 46 months after transplantation for Parkinson's disease. *New England Journal of Medicine* 327, 1549–1555 (1992).

Date, I. Parkinson's disease, trophic factors, and adrenal medullary chromaffin cell grafting: basic and clinical studies. *Brain Research Bulletin* 40, 1–19 (1996).

Luquin, M. R. et al. Recovery of chronic parkinsonian monkeys by autotransplants of carotid body cell aggregates into putamen. *Neuron* 22, 743–750 (1999).

Stoddard, S. L. et al. Decreased adrenal medullary catecholamines in adrenal transplanted parkinsonian patients compared to nephrectomy patients. *Experimental Neurology* 104, 218–222 (1989).

Zawada, W. M. et al. Somatic cell cloned transgenic bovine neurons for transplantation in parkinsonian rats. *Nature Medicine* 4, 569–574 (1998).

Studer, L., Tabar, V. & McKay, R. D. G. Transplantation of expanded mesencephalic precursors leads to recovery in parkinsonian rats. *Nature Neuroscience* 1, 290–295 (1998).

Morrison, S. J., White, P. M., Zock, C. & Anderson, D. J. Prospective identification, isolation by flow cytometry, and in vivo self-renewal of multipotent mammalian neural crest stem cells. *Cell* 96, 737–749 (1999).

Guyton, A. C. & Hall, J. E. Transport of oxygen and carbon dioxide in the blood and body fluids in *Textbook of Medical Physiology* 513–523 (W.B. Saunders, Philadelphia, 1996).

Carnahan, J. F. & Patterson, P. H. Generation of monoclonal antibodies that bind preferentially to adrenal chromaffin cells and the cells of embryonic sympathetic ganglia. *J. Neurosci.* 11, 3493–3506 (1991).

Jessen, K. R. & Mirsky, R. Schwann cells and their precursors emerge as major regulators of nerve development. *Trends in Neurosciences* 22, 402–410 (1999).

Anderson, D. J., Carnahan, J., Michelsohn, A. & Patterson, P. H. Antibody markers identify a common progenitor to sympathetic neurons and chromaffin cells in vivo, and reveal the timing of committment to neuronal differentiation in the sympathoadrenal lineage. *J. Neurosci.* 11, 3507–3519 (1991).

Birren, S. J., Lo, L. C. & Anderson, D. J. Sympathetic neurons undergo a developmental switch in trophic dependence. *Development* 119, 597–610 (1993).

Verdi, J. M. & Anderson, D. J. Neurotrophins regulate sequential changes in neurotrophin receptor expression by sympathetic neuroblasts. *Neuron* 13, 1359–1372 (1994).

Yamamori, Y. et al. The cholinergic neuronal differentiation factor from heart cells is identical to leukemia inhibitory factor. *Science* 246, 1412–1416 (1989).

Guidry, G. L. & Landis, S. C. Developmental regulation of neurotransmitters in sympathetic neurons. *Advances in Pharmacology* 42, 895–898 (1998).

Blancher, C. & Harris, A. L. The molecular basis of the hypoxia response pathway: tumor hypoxia as a therapy target. *Cancer and Metastasis Reviews* 17, 187–194 (1998).

Czyzyk-Krzeska, M. F., Bayliss, D. A., Lawson, E. E. & Millhorn, D. E. Regulation of tyrosine hydroxylase gene expression in the rat carotid body by hypoxia. *Journal of Neurochemistry* 58, 1538–1546 (1992).

Czyzyk-Krzeska, M. F., Furnari, B. A., Lawson, E. E. & Millhorn, D. E. Hypoxia increases the rate of transcription and stability of tyrosine hydroxylase mRNA in pheochromocytoma (PC12) cells. *Journal of Biological Chemistry* 269, 760–764 (1994).

Paulding, W. R. & Czyzyk-Krzeska, M. F. Regulation of tyrosine hydroxylase mRNA stability by protein-binding, pyrimidine-rich sequence in the 3'-untranslated region. *Journal of Biological Chemistry* 274, 2532–2538 (1999).

Holgert, H., Pequignot, J. M., Lagercrantz, H. & Hokfelt, T. Birth-related up-regulation of mRNA encoding tyrosine hydroxylase, dopamine-beta-hydroxylase, neuropeptide tyrosine, and prepro-enkephalin in rat adrenal medulla is dependent on postnatal oxygenation. *Pediatric Research* 37, 701–706 (1995).

Norris, M. L. & Millhorn, D. E. Hypoxia-induced protein-binding to O2-responsive sequences on the tyrosine hydroxylase gene. *Journal of Biological Chemistry* 270, 23774–23779 (1995).

Millhorn, D. E. et al. Regulation of gene expression for tyrosine hydroxylase in oxygen sensitive cells by hypoxia. *Kidney International* 51, 527–535 (1997).

Tian, H., Hammer, R. E., Matsumoto, A. M., Russell, D. W. & McKnight, S. L. The hypoxia-responsive transcription factor EPAS1 is essential for catecholamine homeostasis and protection against heart failure during embryonic development. *Genes & Development* 12, 3320–3324 (1998).

What is claimed is:

1. A method of culturing at least one neural crest stem cell (NCSC) to enhancer survival of said NCSC, said method comprising culturing said NCSC in low oxygen conditions of more than 0.1% and less than 15% $O_2$, wherein said survival is enhanced compared to a control NCSC cultured in ambient oxygen conditions.

2. The method of claim 1, further comprising culturing said NCSC with a mitogen that enhances proliferation.

3. The method of claim 1, further comprising culturing said NCSC with a mitogen that enhances differentiation.

4. The method of claim 1, wherein said at least one neural crest stem cell is cultured from a single isolated cell.

5. The method according to claim 1 wherein said culturing of neural crest stem cell (NCSC) is for at least six hours.

6. A method of culturing at least one neural crest stem cell (NCSC) to enhance survival and proliferation of said NCSC, said method comprising:

(a) culturing said NCSC in low ambient oxygen conditions of more than 0.1% and less than 15% $O_2$, wherein survival is enhanced compared to control NCSC cultured in ambient oxygen conditions; and,
(b) culturing said NCSC from step (a) with a mitogen that enhances proliferation.

7. A method comprising:
culturing at least one neural crest stem cell in low oxygen conditions of more than 0.1% and less than 15% O$_2$ and a mitogen to enhance survival and differentiation of said neural crest stem cell, and,
wherein said differentiation results in a cell that produces a neurotransmitter.

8. The method of claim 7, wherein said neurodegenerative disease is Parkinson's disease.

9. The method of claim 7, wherein said neurodegenerative disease is Alzheimer's disease.

10. A method of culturing at least one neural crest stem cell (NCSC) to form a cell which produces dopamine and norepinephrine, said method comprising culturing said neural crest stem cell in low oxygen conditions of more than 0.1% and less than 15% O$_2$, and further culturing said cell in low oxygen conditions with at least one mitogen, wherein said mitogen is selected from a group consisting of forskolin, bone morphogenetic protein 2 (BMP2), nerve growth factor (NGF), neutrotrophin 3 (NT-3).

11. A method of culturing at least neural crest stem cell (NCSC) to enhance survival and differentiation of said NCSC, said method comprising:
(a) culturing said NCSC in low oxygen conditions of more than 0.1% and less than 15% O$_2$, wherein survival is enhanced compared to a control NCSC cultured in ambient oxygen conditions, and,
(b) culturing said NCSC from step (a) with a mitogen that enhances differentiation.

12. The method of claim 3 or 11, wherein differentiation is to a neuron.

13. The method of claim 3 or 11, wherein differentiation is to a cell of sympathoadrenal lineage.

14. The method of claim 3 or 11, wherein differentiation is to a cell of cholinergic lineage.

15. The method of claim 3 or 11, wherein differentiation is to a sensory neuron.

16. The method of claim 3 or 11, wherein differentiation is to a phenotype which produces dopamine.

17. The method of claim 3 or 11, wherein differentiation is to a phenotype which produces norepinephrine.

18. The method of claim 3 or 11, wherein differentiation is to a phenotype which produces dopamine and norepinephrine.

19. The method of claim 3 or 11, wherein differentiation is to adrenal chromaffin cells.

20. The method of claim 3 or 11, wherein differentiation is to small intensely fluorescent cells.

21. The method of claim 3 or 11, wherein differentiation is to sympathetic neurons.

22. The method of claim 3 or 11, wherein said differentiation is to a phenotype which produces a neurotransmitter wherein deficiency of said neurotransmitter is associated with a neurodegenerative disease.

23. The method according to claim 2 or 11 wherein said mitogen is from serum.

24. The method according to claim 3, 6, or 7 wherein said mitogen is selected from a group consisting of forskolin, bone morphogenetic protein 2 (BMP2), nerve growth factor (NGF), neutrotrophin 3 (NT-3).

* * * * *

UNITED STATES PATENT AND TRADEMARK OFFICE
CERTIFICATE OF CORRECTION

PATENT NO. : 6,759,242 B1
DATED : July 6, 2004
INVENTOR(S) : Csete et al.

It is certified that error appears in the above-identified patent and that said Letters Patent is hereby corrected as shown below:

Column 1,
Line 5, immediately following the title, insert to following:
-- The U.S. Government has certain rights in this invention pursuant to Grant Nos. NIH-5T32GM07616, AR40780, AR42671, AG14435 awarded by the National Institute of Health and Grant No. F49620-98-1-0487 awarded by the Air Force. --

Signed and Sealed this

Twenty-third Day of November, 2004

JON W. DUDAS
*Director of the United States Patent and Trademark Office*